United States Patent [19]

Collen

[11] 4,202,872

[45] May 13, 1980

[54] DETERMINATION OF HEPARIN IN BLOOD PLASMA

[75] Inventor: Désiré J. Collen, Winksele, Belgium

[73] Assignee: Leuven Research & Development V.Z.W., Leuven, Belgium

[21] Appl. No.: 773,192

[22] Filed: Mar. 1, 1977

[30] Foreign Application Priority Data

Mar. 8, 1976 [NL] Netherlands .......................... 7602423

[51] Int. Cl.² ...................... G01N 33/16; A61K 43/00
[52] U.S. Cl. .......................................... 424/1; 424/12; 23/230 B
[58] Field of Search .................. 424/1, 12; 260/112 R; 23/230 B

[56] References Cited

PUBLICATIONS

Merskey et al., Proc. Soc. Exp. Biol. Med., vol. 131, No. 3, Jul., 1969, pp. 871–875.
Einarsson et al., Biochemica et Biphysica Acta, vol. 490, No. 1, Jan., 1977, pp. 104–111.
Collin et al., Thrombosis Research, vol. 7, No. 1, Jul., 1975, pp. 235–238.

*Primary Examiner*—Benjamin R. Padgett
*Assistant Examiner*—Christine M. Nucker
*Attorney, Agent, or Firm*—Lewis H. Eslinger

[57] ABSTRACT

A test for determining the anti-coagulation level in blood samples is based on ascertaining the presence of heparin-antithrombin-III complex therein. This may be done with the aid of antibodies against thrombin-antithrombin-III complex, such antibodies being used e.g. in the form of a latex reagent or a bloodcell reagent.

6 Claims, No Drawings

DETERMINATION OF HEPARIN IN BLOOD PLASMA

The invention relates to a method of determining heparin in blood plasma.

Heparin is a mucopolysaccharide with an average molecular weight of 18.000 which is used pharmacotherapeutically as an antibloodcoagulation agent. After parenteral application, it has immediate antithrombin effect causing inhibition of the modification of fibrinogen into fibrin, and it is, therefore, frequently applied in clinical practice.

For the determination of heparin in blood, biological methods which are rapidly performable and which give good results, are already known. Nevertheless, there is still a need for other methods of determination which may be used in cases where the biological method is less sensitive (for instance in cases of low doses of heparin), or in special cases, for instance if it is desired to determine why the heparin does not work well on a patient, or how the distribution of heparin on antithrombin III and other plasma proteins progresses on a patient.

Experimentation has surprisingly determined that in the presence of heparin in the blood plasma, there arises a positive reaction when combining with antibodies against thrombin-antithrombin III-complex. It was already known that heparin formed a complex with antithrombin III, a known inhibitor of the blood coagulation system. Evidently there appear antigen structures in this way which, anyhow partially, correspond to the antigen structures of thrombin-antithrombin III-complex, so that the heparin-antithrombin III-complex may react with the antibodies against the thrombin-antithrombin III-complex. On the strength of these experiences, a new method of determination for heparin in blood plasma could be devised.

The invention now provides a method of determining heparin in blood plasma characterized in that the presence of heparin-antithrombin III-complex in the blood plasma to be examined is determined in an immunochemical way. By preference, this presence is ascertained with the aid of antibodies against thrombin-antithrombin III-complex. In this manner, the heparin content in blood plasma and thereby also the anticoagulation level in the blood plasma may be determined in a rather simple way.

It is observed that both thrombin and antithrombin III are known components of the blood coagulation system. On the other hand, the thrombin-antithrombin III-complex was detected quite recently only. This thrombin-antithrombin III-complex, and also its insulation from activated blood plasma and the preparation of an antiserum against it, are described in U.S. patent application No. 723,187. In the said application, the possibility of demonstrating the presence of the T-AT-complex in question in blood plasma in an immunochemical way, with the aid of the antiserum or antibodies from it, is indicated. However, it is pointed out emphatically that the antiserum and the antibodies in the said older case served only for the determination of the presence of thrombin-antithrombin III-complex, whereas the present invention is precisely directed to the determination of the heparin-antithrombin III-complex in blood plasma.

In principle, the method of determination according to the invention may be carried out in various manners. By preference, however, the method of determination is carried out by combining the blood plasma to be examined with a latex of particles of synthetic resin or a suspension of bloodcells, which particles or which cells bear antibodies against thrombin-antithrombin III-complex on their surface and then ascertaining whether or not agglutination results (direct agglutination test). In actual practice, various dilutions of the blood plasma to be examined will be prepared and then it will be ascertained at which dilution agglutination still arises. From the dilution found a certain number is obtained which is called the titre of the blood plasma. From the titre, the amount of heparin in the blood plasma may be calculated by comparison with the titres of blood plasma to which known amounts of heparin have been added. If the antibodies of the reagent used have been well purified in advance, a great difference between the titres in a positive and a negative outcome and thus a well applicable method of determination may be achieved.

Of course, the antibodies of the reagent used should be prepared and purified without heparin being present seeing that otherwise the power of reaction with heparin-antithrombin III-complex might be lost.

In the course of experiments with the method of determination according to the invention, it has been found that in specific instances a false positive outcome is obtained, namely if the blood plasma to be examined comprises thrombin-antithrombin III-complex. The explanation is that both the T-AT-complex and the Hep-AT-complex may react with the antibodies against the T-AT-complex due to which disturbance of the desired reaction may arise.

This false positive outcome can, however, be avoided by carrying out, apart from the actual determination test, a check test in which the blood plasma to be examined is also combined with a latex of particles of synthetic resin or a suspension of bloodcells which particles or cells bear antibodies against the thrombin-antithrombin III-complex on the surface and then ascertaining whether or not agglutination arises. The difference is here that the antibodies for the check test have been prepared and purified in the presence of heparin, i.e. incubated with heparin-AT-complex, due to which the power to react with Hep-AT-complex in a subsequently agglutination test has been lost. The antibodies treated with heparin may react with T-AT-complex in the check test and, therefore, if in the course of the check test a positive outcome with almost the same titre as in the course of the actual determination test is found, it is evident that the test only indicates the presence of T-AT-complex in the blood plasma. On the other hand, if in the course of the check test a negative outcome is found whereas the actual determination test indicated a positive outcome, heparin was decidedly present in the blood plasma.

It has been found that also blood plasma of a patient with rheumatism factor in the blood may give a false positive outcome of the determination test. By treatment of the blood plasma to be examined with insolubilized human gamma-globulins this rheumatism factor may be removed entirely from the blood plasma after which the remaining plasma is suitable for the performance of the method of determination.

The method of determination according to the invention may serve not only for the qualitative determination of heparin in blood plasma but, to a certain extent, also for a quantitative determination thereof. Namely, as will be evident from the examples, at increasing heparin concentration, the titre of the blood plasma increases proportionally with the increase of the concentration.

For the performance of the diagnosis test according to the invention a special latex- or bloodcell-reagent is required. This may be prepared by combining a latex of particles of synthetic resin or a suspension of red bloodcells with an antiserum generated against thrombin-antithrombin III-complex, so that the antibodies from this antiserum may become attached to the surface of the particles of synthetic resin or bloodcells.

The required antiserum against thrombin-antithrombin III-complex may be prepared in the customary way by injecting rabbits with the complex in question, drawing blood regularly from the rabbits and collecting the bloodserum from the blood drawn. Then the antiserum may be purified by various methods, such as chromatography over insolubilized blood plasma (in which the filtrate is further used). By preference, however, the antiserum is purified by immunoprecipitation with fresh human blood plasma followed up by chromatography over an insolubilized thrombin-antithrombin III-complex, thus obtaining an antiserum which remains stable for a long time.

Purification of the antiserum may be carried out both in the presence and in the absence of heparin, so as to obtain antibodies for the check test later on respectively the actual determination test. This heparin is then, for example, added to the human blood plasma during the immunoprecipitation in the preferred method of purification applied.

The thrombin-antithrombin III-complex required may be obtained by insulation from blood plasma of which the coagulation mechanism has been activated. This insulation is carried out, for example, by affinity chromatography on heparin-Sephadex and gelfitration on Ultrogel AcA 22.

Furthermore, it is observed that the methods of preparing and purifying the T-AT-complex, the antiserum and the latex- or bloodcell-reagent as such do not constitute part of the present invention. These methods and their results are claimed elsewhere.

In the following examples the method of determination is preceded by examples of the purification, insulation and preparation of the reagent required and the materials needed for these purposes, in order to give a complete picture of the possibilities. It will, however, be clear that these examples are not meant to be exhaustive.

EXAMPLE I

INSULATION OF THROMBIN-ANTITHROMBIN III-COMPLEX FROM BLOOD PLASMA.

The thrombin-antithrombin III-complex was insulated from blood plasma defibrinated with reptilase, the coagulation mechanism of which was activated in the intrinsic way. Insulation was performed by affinity chromatography on heparin-Sepharose and gelfiltration on Ultrogel AcA 22.

Starting materials. Bloodbank plasma from normal donors caught on ACD-coagulant served as starting material. For defibrination reptilase (Defibrase of Pentapharm, Basle) was used whilst for the activation of the coagulation system calciumchloride and phospholipide (Thrombofax, of Ortho Pharmaceutical Company) was used. Further, use was made of radioactive marked prothrombin obtained by marking purified human prothrombin with $^{125}I$ in the manner of McFarlane (see Nature, (London) 182, 53 1958).

Activation. Defibrase in an amount of 1 ml per liter was added to portions of 2 liters of blood plasma, after which the plasma was made coagulate for 4 hours at 37° C. and for one night in a cold room. The fibrin formed was removed gradually by rolling up on a glass bar. Traces of $^{125}I$-prothrombin were added to the defibrinated plasma, after which the coagulation system was activated by adding 28 ml of 1 M $CaCl_2$ and 40 ml of Thrombofax per liter of defibrinated plasma. The activation of the coagulation system was followed up on the strength of the gradual reduction of the prothrombin present. After about 1 hour the remaining amount of prothrombin was less than 5%.

Insulation. For the affinity chromatography use was made of heparin-Sepharose which was washed and equilibrated with 0,1 M tris-HCl, .15 M NaCl, 0,01 M citrate buffer of pH 7.5. 150 Ml of this heparin-Sepharose (volume after sedimentation) was mixed with 2000 ml of the blood plasma defibrinated and activated in the above way, for 2 hours at room temperature. Then the gel was washed on a Buchner funnel with 3 liters of equilibration buffer and poured into a column. The absorbed material was eluted with a saltgradient comprising 500 ml of 0,01 M tris-HCl, 0,15 M NaCl, 0,01 M citrate, pH=7,5, as a starting buffer, and 0,01 M tris-HCl, 1 M NaCl, 0,01 M citrate, pH=7,5 as an end-buffer. Thus three different fractions were obtained: (1) lipoproteins which eluted particularly at the beginning of the gradient and the amounts of which varied from preparation to preparation; (2) a thrombin-antithrombin III-complex demonstrated by simultaneous elution of $^{125}I$ and an antigen related to antithrombin III at a salt concentration of about 0,4 M, and (3) remaining antithrombin III eluted after the peak of the foregoing fraction.

The thrombin-antithrombin III-fractions of various tests were combined and concentrated by ultrafiltration. At this stage the preparation was contaminated with lipoproteins as was evident from its turbidity in solution and its slight mobility in a polyacrylamide gel. Therefore, the preparation was further purified by gel filtration on a column of Ultrogel AcA 22 of 2,5×45 cm, equilibrated with a buffer of 0,1 M NaCl, 0,05 M phosphate, 0.02% azide, pH=7,5. Hereby the lipoproteins eluted near the empty volume of the column. The thrombin-antithrombin-complex (hereafter indicated as T-AT) which, after purification, showed a tendency to coacervate, eluted in a broad peak. The free antithrombin III eluted later. The T-AT-fractions of various tests localized by measuring $^{125}I$ and of an antigen related with antithrombin III, were combined and concentrated by vacuum dialysis. The average proceeds of 4 insulation tests, each starting from 2 liters of blood plasma, amounted to 25 units O.D. per liter of plasma.

Identification. By electrophoresis of T-AT on a SDS-polyacrylamide gel a sharp protein band with a molecular weight of around 65.000 (free antithrombin III) was obtained as also hazy bands with slower migration. After reduction with DTT, three sharp bands with molecular weights between 65.000 and 95.000, among which bands of antithrombin III and of thrombin-antithrombin III, were observed.

EXAMPLE II

PREPARATION OF ANTISERUM.

Preparation. Rabbits were immunized with thrombin-antithrombin III-complex (4 rabbits). For this purpose, the complex was solved in a 0,15 M kitchen-salt-solution to a concentration of 0,2 mg per ml and mixed with 1 ml of complete Freund's adjuvant. Of this mixture 1 ml was injected per rabbit, distributed in the soles of the feet, the subcutaneous tissue in the neck and the thigh muscles. Then three times, each time at an interval of 1 or 2 weeks, an equal amount of antigen mixed with incomplete Freund's adjuvant and distributed on the subcutaneous and intermuscular way, was administered. Commencing one week after the fourth injection, twice per week 30–80 ml of blood was drawn by punction of the ear arteries. The serum of 3 or 4 consecutive blood-drawings was each time combined and further jointly worked up. The titre of the antiserum was determined by a hemagglutination test. For a period of 3 months up to 500 ml of serum was obtained per rabbit.

Determination of the titre. For the performance of the agglutination test a special reagent was prepared comprising red bloodcells bearing purified complex of the T-AT-type on the surface. This reagent was made by tanning human red bloodcells of the O group and then combining with the purified complex in the manner described by Merskey et al for fibrinogen breakdown products (see Proc. Soc. Exp. Biol. Med. 131,871, 1969). Two units O.D. of the T-AT-complex solved in 100 ml of citrate phosphate buffer were used. The reagent was stored at 4° C. and used within the month.

Of the antiserum various dilutions were made, after which each of the dilutions was combined with a reagent to match, after which the appearance, either or not, of hemagglutination was observed. The highest dilution in which still clearly visible hemagglutination appeared, was taken as titre of the antiserum. The values obtained were found to be strongly divergent, dependent on the experimental animals used and on the moment of blooddrawing.

EXAMPLE III

PURIFICATION OF ANTISERUM.

An antiserum against thrombin-antithrombin III-complex was purified by immunoprecipitation of non-specific antibodies with the aid of fresh human blood plasma followed up by chromatogaphy over a column of insolubilized thrombin-antithrombin III-complex.

Starting materials. An antiserum obtained according to example II served as the starting material. In the first step, fresh human blood plasma was used, namely bloodbank plasma from normal donors, caught on ACD-anticoagulant, and further the material para-nitrophenyl-para-guanidinobenzoate (p-NGB, of Cyclo Chemical Company). In the chromatography use was made of a column of insolubilized purified T-AT-complex, the preparation of which is described below. The T-AT-complex needed for this purpose was prepared according to example I.

Immunoprecipitation of non-specific antibodies. To 5 ml of antiserum p-NGB was added to an end-concentration of $10^{-5}$ M and subsequently 2 ml of fresh human blood plasma. After 30 minutes stirring at room temperature the precipitate obtained was removed by separation. The remaining fluid was used for the column chromatography.

Preparation of insolubilized thrombin-antithrombin III complex.

30 ml of agarose (sedimented volume) activated with 3 grams of CNBr was mixed with 70 ml of coupling buffer (0,1 M $NaHCO_3$-0,5 M NaCl, pH=9,0) and 20 units of O.D. (at 280 nm) of the thrombin-antithrombin III-complex. About 75% of the protein complex was bonded to the agarose. From this product a chromatographic column of 0,9×15 cm was built up.

Chromatography. The remaining fluid of the antiserum was carried over a column of the thrombin-antithrombin III-complex prepared as above, at a speed of 10 ml/cm²/hour, which column was equilibrated with a NaCl-phosphate buffer. (0,1 M NaCl—0,05 M $Na_2HPO_4$, pH=7,5). The non-absorbed proteins were carefully washed out with equilibration buffer. Then the bonded antibodies were eluted with 3 M $NH_4SCN$. The eluents collected were dialyzed against the equilibration buffer and concentrated by vacuum dialysis.

Finally 3,5 ml of purified antiserum (solution of specific antibodies against thrombin-antithrombin III-complex) with an O.D. of 1,75 at 280 nm was obtained. At geldiffusion, this antiserrum did not show a clear reaction with fresh haparinfree blood plasma, but it did show clear precipitin lines with fresh bloodserum. It was suitable as an antiserum for application of an agglutination-inhibiting test.

EXAMPLE IV

PURIFICATION OF ANTISERUM.

The method of example III was repeated with the difference that in the immunoprecipitation, use was made of fresh human blood plasma to which heparin was added before. This heparin (Liquemine, of Hoffmann La Roche, a solution with 5000 IU per ml) was used in an amount of 3 IU per ml of blood plasma. After removal of the precipitate obtained the remaining fluid was submitted to column-chromatography in the same manner as in example III. Finally 3,5 ml of purified antiserum with an O.D. of 175 at 280 nm was obtained. In geldiffusion this solution did not show a clear reaction with fresh blood plasma, but it did show clear precipitin lines with fresh bloodserum.

EXAMPLE V

LATEX-REAGENT FOR THE DIAGNOSIS TEST.

A special reagent for carrying out the clinical diagnosis test was prepared by providing particles of synthetic resin with specific antibodies against T-AT-complex on the surface.

A latex of particles of synthetic resin (Bacto-Latex of Difco Laboratories, Detroit, Mich. USA) was washed twice with a buffer solution (0,02 M glycin, 0.03 M NaCl, pH=9,0), after which the particles were separated off (Sorvall RC2, 10.000 rpm, 5 min.) and resuspended in the same buffer solution (1,6 time the original volume). An amount of 0.1 ml of purified antiserum, obtained according to Example III, was added per milliliter of suspension and mixed at room temperature for 60 minutes. The coated particles of synthetic resin were separated off, washed with a buffer solution (0,02 M glycin, 0,03 M NaCl, pH=9,0) and resuspended in another buffer solution (0,1 M glycin, 0,15 M NaCl, pH=9,0), to which 1% of cow's albumin (Povite, Amsterdam) and 0,1% of sodiumazide were added. The reagent obtained was suitable for performing a direct agglutination test.

EXAMPLE VI

LATEX-REAGENT FOR DIAGNOSIS TEST.

The method of example V was repeated with the difference that this time an antiserum purified according to example IV was used. The latex-reagent obtained was suitable for carrying out a direct agglutination test.

EXAMPLE VII

PERFORMANCE OF THE DIAGNOSIS TEST.

For carrying out the diagnosis test always two tests were made, namely the actual determination test with a latex reagent of example V and a check test with the latex reagent of example VI. In both cases, various dilutions of the blood plasma sample to be examined were made in a buffer solution (0,1 M glycin, 0,15 M NaCl, 1% of albumin, pH=9,0). On a small black plate 20 microliters of each of the dilutions or of the buffer solution alone (blanc test) were mixed with 20 µl of the latex reagent in question. The suspension was mixed continuously sloping the plate to and fro and the agglutination was read after 3 minutes (+ or −) and after 5 minutes (+ or −). Then the determination test and the check test were compared with each other.

EXAMPLE VIII

OUTCOMES OF THE DIAGNOSIS TEST.

A. Fresh blood plasma of 40 sound persons agglutinated the latex particles of example V and VI in dilutions of ½ to ⅛ so that the titre was 2–8. On the other hand, a purified T-AT-complex (in a concentration of 10 mg per 100 ml) shew in both cases a titre of 160–320. In the serum of fresh blood caught in a glass tube and incubated at room temperature, there arose an agglutinating activity progressing progressively and parallel to the decrease of the thrombin concentration which, after 90 minutes, had reached a titre of 320–640.

B. In the presence of thrombin-antithrombin III-complex in the blood plasma to be examined, a false positive outcome was obtained which, with the aid of the check test, could be demonstrated as such. So, in the determination test with the latex-reagent of example V, the blood plasma of three hospital-patients who, according to hemostase examination showed a slow intervascular coagulation, gave an agglutinating activity with a titre of respectively 32, 64 and 96. In the check test with the latex-reagent of example VI the same outcome was obtained, which indicates unambiguously the presence of T-AT-complex in the blood plasma.

C. Fresh blood plasma of a patient with rheumatism-factor in the serum was also found to generate agglutination of the latex particles and, therefore, a high titre. By treatment of the blood plasma with insolubilized human gamma-globulins, this agglutinating action, contrary to the action generated by the coagulation of the blood, could be removed.

D. When heparin was added to the fresh blood plasma, a clear positive outcome was obtained since the determination test with the latex-reagent of example V showed an increased titre and the check test with the latex-reagent of example VI did not show an increase of the titre. The titre in the actual determination test, which on the outset was 2–8, increased in proportion to the heparin concentration in the blood plasma and reached a maximum of 160 at a concentration of 2–10 IU of heparin per ml of blood plasma. In the case of higher heparin concentrations (10–50 IU per ml.) the titre decreased again. This gives a possibility of quantitative determination.

What I claim is:

1. A method of determining heparin in blood plasma comprising contacting the blood plasma to be examined with antibodies to thrombin-antithrombin-III complex to cause reaction between heparin-antithrombin III complex and the said antibodies to thrombin-antithrombin-III complex, observing an onset of reaction, and determining presence of heparin from such observation by comparison with blood plasmas of known heparin content.

2. A method of determining an anti-coagulation level in human blood plasma, which comprises effecting the method as claimed in claim 1 and calculating said anti-coagulation level from its results, said anti-coagulation level being correlated to heparin concentration in the blood.

3. A method according to claim 1, wherein the blood plasma to be tested for heparin is combined with a latex of particles of synthetic resin or a suspension of blood-cells, which particles or which cells bear said antibodies against thrombin-antithrombin III-complex on their surface.

4. A method according to claim 3, wherein the antibodies are prepared and purified without the presence of heparin.

5. A method according to claim 4, wherein a check test is carried out on the determination by combining the blood plasma to be examined with a latex of particles of synthetic resin or a suspension of blood cells which particles or cells bear antibodies against thrombin-antithrombin III-complex on their surface, the antibodies for the check test having been prepared and purified in the presence of heparin; and then determining whether or not agglutination arises.

6. A method according to claim 3, wherein the antibodies for the determination are prepared by purifying an antiserum generated against thrombin-antithrombin III-complex by immunoprecipitation with fresh human blood plasma, followed by chromatography over an insolubilized thrombin-antithrombin III-complex.

* * * * *